US00PP17937P2

(12) United States Plant Patent
Uchneat

(10) Patent No.: US PP17,937 P2
(45) Date of Patent: Aug. 21, 2007

(54) ***IMPATIENS* PLANT NAMED 'BALFIESTARSA'**

(50) Latin Name: *Impatiens walleriana*
Varietal Denomination: Balfiestarsa

(75) Inventor: Michael S. Uchneat, Geneva, IL (US)

(73) Assignee: Ball Horticultural Company, West Chicago, IL (US)

( * ) Notice: Subject to any disclaimer, the term of this patent is extended or adjusted under 35 U.S.C. 154(b) by 54 days.

(21) Appl. No.: 11/298,057

(22) Filed: Dec. 9, 2005

(51) Int. Cl.
*A01H 5/00* (2006.01)

(52) U.S. Cl. ..... Plt./317

(58) Field of Classification Search ..... Plt./317, Plt./319
See application file for complete search history.

(56) References Cited

PUBLICATIONS

European Plant Breeders' Rights application No. 2005/2003 filed Oct. 25, 2005.

*Primary Examiner*—Howard J. Locker
(74) *Attorney, Agent, or Firm*—Audrey Charles

(57) ABSTRACT

A new and distinct cultivar of *Impatiens* plant named 'Balfiestarsa', characterized by its double-type salmon-colored flowers with light red-colored mottling, dark green-colored foliage, and vigorous, upright mounded growth habit.

1 Drawing Sheet

Latin name of genus and species of plant claimed: *Impatiens walleriana.*
Variety denomination: 'Balfiestarsa'.

BACKGROUND OF THE INVENTION

The present invention relates to a new and distinct cultivar of *Impatiens* plant botanically known as *Impatiens walleriana* and hereinafter referred to by the cultivar name 'Balfiestarsa'.

The new cultivar originated in a controlled breeding program in Elburn, Ill. during February 2003. The objective of the breeding program was the development of new compact *Impatiens* cultivars with fully double-type flowers, attractive flower and foliage coloration, and freely branching growth habit.

The new cultivar was the result of a self-pollination of the proprietary *Impatiens walleriana* breeding selection 3596-3-2, not patented, characterized by its white-colored flowers with coral-colored venation, medium green-colored foliage, and medium vigorous habit. The new cultivar was discovered and selected by the inventor as a single flowering plant within the progeny of the above stated self-pollination during October 2003 in a controlled environment at Elburn, Ill.

Asexual reproduction of the new cultivar by terminal stem cuttings since October 2003 at Elburn, Ill. and West Chicago, Ill. has demonstrated that the new cultivar reproduces true to type with all characteristics, as herein described, firmly fixed and retained through successive generations of such asexual propagation.

SUMMARY OF THE INVENTION

The following characteristics of the new cultivar have been repeatedly observed and can be used to distinguish 'Balfiestarsa' as a new and distinct cultivar of *Impatiens* plant:

1. Double-type, salmon-colored flowers with light red-colored mottling;
2. Dark green-colored foliage; and
3. Vigorous, upright mounded growth habit.

Plants of the new cultivar differ from plants of the parent primarily in flower color, foliage color and growth habit.

Of the many commercially available *Impatiens* cultivars known to the inventor, the most similar in comparison to the new cultivar is 'Salmon Sunrise', U.S. Plant Pat. No. 9,691. However, in side by side comparisons, plants of the new cultivar differ from plants of 'Salmon Sunrise' in the following characteristics:

1. Plants of the new cultivar are less floriferous than plants of 'Salmon Sunrise'; and
2. Plants of the new cultivar have a lighter flower color than plants of 'Salmon Sunrise'.

BRIEF DESCRIPTION OF THE PHOTOGRAPHS

The accompanying photographs show, as nearly true as it is reasonably possible to make the same color illustrations of this type, typical flower and foliage characteristics of the new cultivar. Colors in the photographs differ slightly from the color values cited in the detailed description, which accurately describes the colors of 'Balfiestarsa'. The plants were grown in 10 cm pots for 6 weeks in a greenhouse at West Chicago, Ill.

DETAILED BOTANICAL DESCRIPTION

Figure 1:
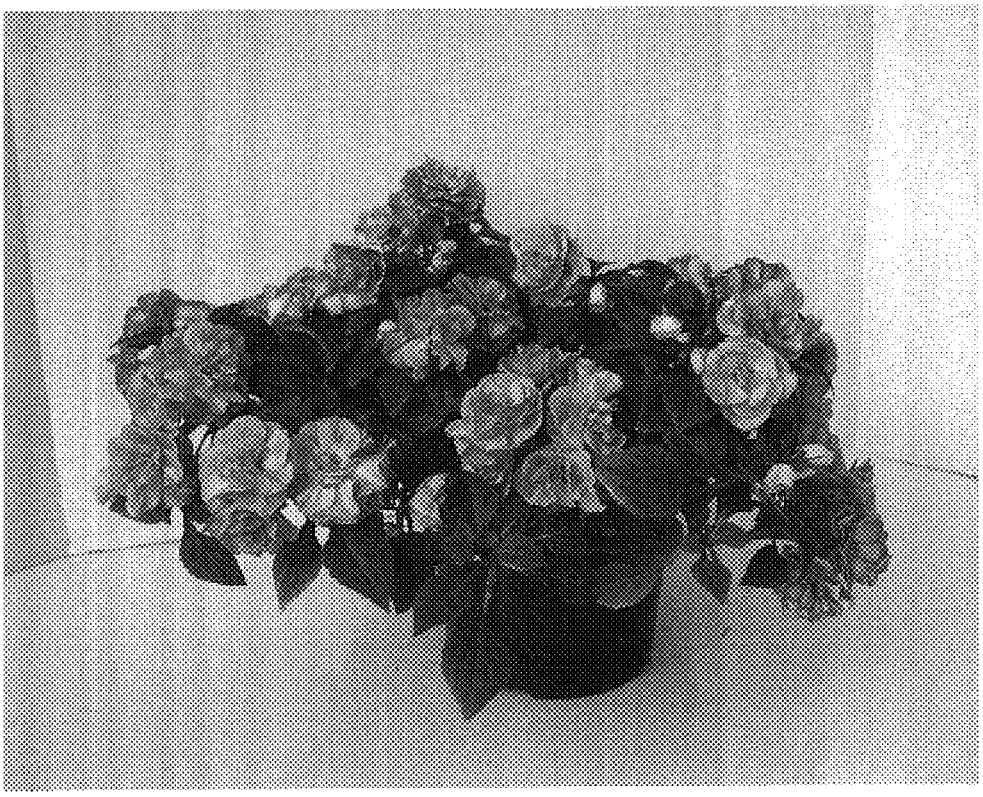
FIG. 1 illustrates a side view of the overall growth and flowering habit of 'Balfiestarsa'.
Figure 2:
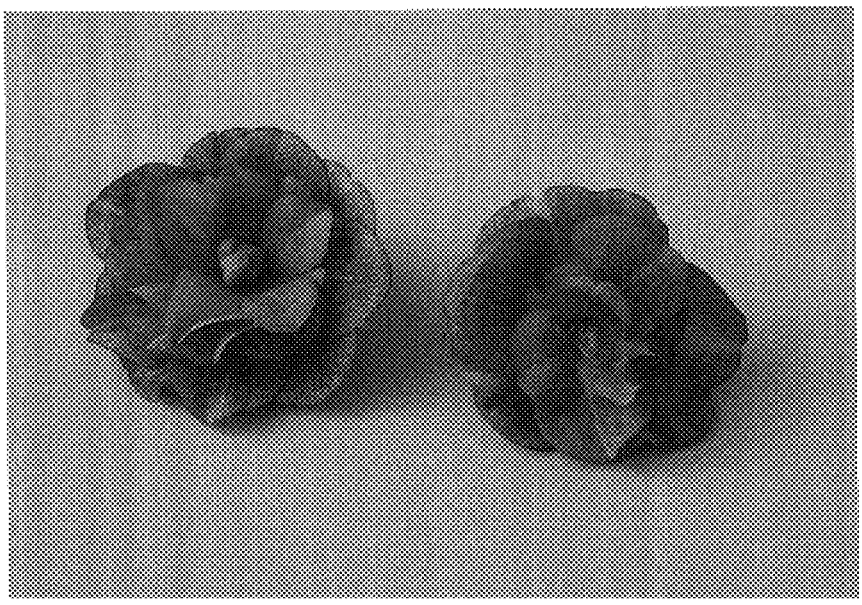
FIG. 2 illustrates a close-up view of a partially open flower on the left and a fully open flower on the right of 'Balfiestarsa'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2001 edition, except where general color terms of ordinary significance are used. The color values were determined on Jul. 6, 2005 between 3:00 p.m. and 4:00 p.m. under natural light conditions, in West Chicago, Ill.

The following descriptions and measurements describe plants produced from cuttings taken from stock plants and grown in a double polycarbonate-covered greenhouse under conditions comparable to those used in commercial practice. The plants were grown at West Chicago, Ill. in 10 cm pots for 6 weeks utilizing a soilless growth medium. Greenhouse temperatures were maintained at approximately 65° F. to 75° F. (18° C. to 24° C.) during the day and approximately 55° F. to 62° F. (13° C. to 17° C.) during the night. Greenhouse light levels of 4,000 to 6,000 footcandles were maintained during the day.

Botanical classification: *Impatiens walleriana* cultivar Balfiestarsa.

Parentage:

*Female parent.*—Proprietary *Impatiens walleriana* breeding selection 3596-3-2, not patented.

*Male parent.*—Proprietary *Impatiens walleriana* breeding selection 3596-3-2, not patented.

Propagation:

*Type cutting.*—Terminal stem.

*Time to initiate roots.*—Approximately 7 to 8 days.

*Time to produce a rooted cutting.*—Approximately 21 to 28 days.

*Root description.*—Fine and fibrous.

*Rooting habit.*—Freely branching.

Plant description:

*Crop time.*—Approximately 6 to 9 weeks from a rooted cutting.

*Growth habit and general appearance.*—Vigorous, upright and mounded.

*Size.*—Height from soil level to top of plant plane: Approximately 20.2 cm. Width: Approximately 39.1 cm.

*Branching habit.*—Freely basal branching. Approximately 4 branches per plant.

*Branch.*—Strength: Strong. Length: Approximately 19.2 cm. Diameter: Approximately 8.9 mm. Texture: Glabrous. Color: Closest to 147C with streaks of 187B. Internode length at center of branch: Approximately 2.2 cm.

*Foliage.*—Number of leaves per main branch: Approximately 14. Fragrance: None. Form: Simple. Arrangement: Alternate. Aspect: Acute angle to stem. Shape: Ovate. Margin: Crenate, ciliate. Apex: Mucronate. Base: Attenuate. Venation pattern: Pinnate. Length of leaf at center of stem: Approximately 4.4 cm. Width of leaf at center of stem: Approximately 2.9 cm. Texture of upper and lower surfaces: Glabrous. Color of upper surface of mature foliage: Closest to 139A with venation of 143C. Color of lower surface of mature foliage: Closest to 138B with splotches of closest to 185C and venation of 143B. Petiole length: Approximately 2.6 cm. Petiole diameter: Approximately 3.0 mm. Petiole texture: Glabrous. Color of upper surface of petiole: 138C with streaks of 70A. Color of lower surface of petiole: 138C.

Flowering description:

*Flowering habit.*—'Balfiestarsa' is freely flowering under outdoor growing conditions with substantially continuous blooming from spring through autumn and year round in greenhouse environment.

*Time to first flower.*—Approximately 10 weeks from sticking of unrooted cutting.

*Lastingness of individual bloom.*—Approximately 7 to 9 days.

Flower description:

*Type.*—Double. Borne: Above foliage. Quantity of fully open flowers per plant at 6 weeks: Approximately 11. Fragrance: None.

*Bud rate of opening.*—Generally takes 3 to 4 days for bud to progress from first color to fully open flower.

*Bud just before opening.*—Shape: Oval. Quantity showing color at six weeks: Approximately 13. Length: Approximately 1.5 cm. Diameter: Approximately 1.1 cm. Color: Closest to 55D with dusting of 54B near margin and margin of solid 54B.

*Corolla.*—Shape: Hemispherical. Diameter: Approximately 4.2 cm. Depth: Approximately 2.3 cm.

*Petals.*—Quantity: 26. Shape: Obovate. Aspect: Flat. Appearance: Iridescent. Margin: Entire. Apex: Obtuse, some are emarginate. Base: Attenuate. Texture: Glabrous. Length of outermost petal: Approximately 2.3 cm. Width of outermost petal: Approximately 2.1 cm. Length of innermost petal: Approximately 1.2 cm. Width of innermost petal: Approximately 7.4 mm. Color of upper surface of petals when fully open: Base and background of N155C with margin of 54A, mottling of 54A and 54B over one-half of the surface inside the margin, and venation at base of 71A. Color of lower surface of petals when fully open: Base and background of N155C with margin of 54B and mottling of 54B and 54C over one-half of the surface inside the margin.

*Spur.*—Quantity: One primary and 3 to 4 vestigial per flower. Length of primary spur: Approximately 2.7 cm. Diameter of primary spur at tip: Approximately 0.7 mm. Diameter at base: Approximately 1.9 mm. Texture: Glabrous. Color: 59A at distal end and 147D at proximal end with streaks of 59A that radiate from the distal end throughout three fourths of the length.

*Peduncle.*—Strength: Strong. Aspect: Acute angle to stem. Length: Approximately 1.6 cm. Diameter: Approximately 1.5 mm. Texture: Glabrous. Color: Closest to 147C.

*Calyx.*—Quantity of sepals per flower: 4. Upper sepal is fused to lower surface of upper petal. Apex: Acuminate. Texture of upper and lower surfaces: Glabrous. Shape of lateral sepal: Lanceolate. Length of lateral sepal: Approximately 2.8 mm. Width of lateral sepal: Approximately 1.3 mm. Color of lateral sepal: 143B with 70A at tip. Shape of lower sepal: Ovate. Length of lower sepal: Approximately 1.2 cm. Width of lower sepal: Approximately 8.3 mm. Color of lower sepal: 150D.

*Reproductive organs.*—None observed.

Seed and fruit production: Neither seed nor fruit production has been observed.

Disease and pest resistance: Resistance to pathogens and pests common to *Impatiens* has not been observed.

What is claimed is:

1. A new and distinct cultivar of *Impatiens* plant named 'Balfiestarsa', substantially as herein shown and described.

* * * * *